(12) United States Patent
Krueger (10) Patent No.: US 10,711,852 B1
(45) Date of Patent: Jul. 14, 2020

(54) LOCKING CLUTCH SYSTEMS

(71) Applicant: General Electric Company, Schenectady, NY (US)

(72) Inventor: Paul Jason Krueger, Pewaukee, WI (US)

(73) Assignee: General Electric Company, Schenectady, NY (US)

(*) Notice: Subject to any disclaimer, the term of this patent is extended or adjusted under 35 U.S.C. 154(b) by 0 days.

(21) Appl. No.: 16/252,197

(22) Filed: Jan. 18, 2019

(51) Int. Cl.
*F16D 41/08* (2006.01)
*A61B 5/055* (2006.01)
*F16D 41/067* (2006.01)
*F16D 15/00* (2006.01)

(52) U.S. Cl.
CPC ............ *F16D 41/088* (2013.01); *A61B 5/055* (2013.01); *F16D 15/00* (2013.01); *F16D 41/067* (2013.01)

(58) Field of Classification Search
CPC ...... F16D 41/088; F16D 41/067; F16D 15/00; A61B 5/055; A61B 6/0407; A61G 13/122; A61G 13/04
See application file for complete search history.

(56) References Cited

U.S. PATENT DOCUMENTS

| 3,269,496 | A | 6/1966 | Kilness |
| 3,265,171 | A | 8/1966 | Kilness |
| 5,669,476 | A * | 9/1997 | Lederman ............ F16D 41/067 188/82.84 |
| 6,487,735 | B1 * | 12/2002 | Jacques, II ............ A47D 7/02 5/424 |
| 8,904,907 | B2 | 12/2014 | Douglass |
| 2007/0246318 | A1 * | 10/2007 | Shirataki ............... F16D 41/067 192/45.01 |
| 2009/0242346 | A1 * | 10/2009 | Kinoshita ............. F16D 41/088 192/45.019 |
| 2017/0001714 | A1 * | 1/2017 | Piaton ..................... F16D 27/00 |
| 2018/0135706 | A1 * | 5/2018 | Stoltze ................ F16D 43/2028 |
| 2018/0177468 | A1 | 6/2018 | Lubar et al. |

* cited by examiner

*Primary Examiner* — David J Hlavka
(74) *Attorney, Agent, or Firm* — The Small Patent Law Group LLC; Dean D. Small (57) ABSTRACT

A clutch assembly includes an inner hub, an outer hub, a roller bearing, and a control collar. The inner hub includes a cam surface having a peak and a bottom. The roller bearing is interposed between the inner and outer hub and coupled to the inner hub at a predetermined position relative to the peak. In a locked position, the roller bearing is proximate the peak, wherein rotation of the inner hub relative to the outer hub is inhibited in a locked direction. In the unlocked position, the roller bearing is disposed a greater distance from the peak relative to the locked position, wherein rotation of the inner hub relative to the outer hub is not inhibited in the locked direction.

20 Claims, 5 Drawing Sheets

LOCKING CLUTCH SYSTEMS

BACKGROUND OF THE INVENTION

The subject matter disclosed herein relates generally to apparatus and methods for providing a locking clutch assembly, for example a locking clutch assembly configured to control movement of a table arm for a medical imaging system.

Lockable clutches may be used in a variety of contexts. In some applications, it may be desirable to have a clutch that is locking or lockable over one range or direction, but free to rotate over another range or direction. For example, an arm board on a patient table for medical imaging may be required to be lockable in one direction over a first range but not over a second range. It may be impractical or challenging for an operator to access or utilize a locking mechanism for releasing a lock over the second range. Further, currently available one-way clutches that satisfy loading requirements for a medical imaging table arm may be impractically large, and additionally may utilize ferrous materials that present drawbacks in a magnetic resonance imaging context.

BRIEF DESCRIPTION OF THE INVENTION

In one example embodiment, a clutch assembly is provided that includes an inner hub, an outer hub, a roller bearing, and a control collar. The inner hub is rotatable about a hub axis, and includes a cam surface having a peak and a bottom. The outer hub is concentric with and disposed radially outward of the inner hub, with the inner hub rotatable about the hub axis with respect to the outer hub. The roller bearing is interposed between the inner and outer hub. The roller bearing is coupled to the inner hub at a predetermined position relative to the peak. The control collar is configured to move the roller bearing between a locked position and an unlocked position. In the locked position, the roller bearing is proximate the peak, wherein rotation of the inner hub relative to the outer hub is inhibited in a locked direction but not uninhibited in an unlocked direction. In the unlocked position, the roller bearing is disposed a greater distance from the peak relative to the locked position, wherein rotation of the inner hub relative to the outer hub is not inhibited in the locked direction or the unlocked direction.

In another example embodiment, a clutch assembly is provided that includes an inner hub, an outer hub, a roller bearing, and a control collar. The inner hub is rotatable about a hub axis, and includes a cam surface having a peak and a bottom. The outer hub is concentric with and disposed radially outward of the inner hub, with the inner hub rotatable about the hub axis with respect to the outer hub. The roller bearing is interposed between the inner and outer hub. The roller bearing is coupled to the inner hub at a predetermined position relative to the peak. The control collar is configured to move the roller bearing between a locked position and an unlocked position. In the locked position, the roller bearing is proximate the peak, wherein rotation of the inner hub relative to the outer hub is inhibited in a locked direction but not uninhibited in an unlocked direction. In the unlocked position, the roller bearing is disposed a greater distance from the peak relative to the locked position, wherein rotation of the inner hub relative to the outer hub is not inhibited in the locked direction or the unlocked direction. A recess extends into an inner surface of the outer hub and defines a free range in which the inner hub is free to rotate relative to the outer hub (e.g, where position of the control collar is inconsequential).

In another example embodiment, a medical imaging table assembly is provided that includes a table bed, a table arm, and a clutch assembly. The table arm is rotatably coupled to the table bed with the clutch assembly. The clutch assembly includes an inner hub, an outer hub, a roller bearing, and a control collar. The inner hub is rotatable about a hub axis, and includes a cam surface having a peak and a bottom. The outer hub is concentric with and disposed radially outward of the inner hub, with the inner hub rotatable about the hub axis with respect to the outer hub. The table arm is coupled to one of the inner hub or the outer hub, and the table bed is coupled to the other of the inner hub or the outer hub. The roller bearing is interposed between the inner and outer hub. The roller bearing is coupled to the inner hub at a predetermined position relative to the peak. The control collar is configured to move the roller bearing between a locked position and an unlocked position. In the locked position, the roller bearing is proximate the peak, wherein rotation of the inner hub relative to the outer hub is inhibited in a locked direction but not uninhibited in an unlocked direction. In the unlocked position, the roller bearing is disposed a greater distance from the peak relative to the locked position, wherein rotation of the inner hub relative to the outer hub is not inhibited in the locked direction or the unlocked direction.

DETAILED DESCRIPTION OF THE INVENTION

The following detailed description of certain embodiments will be better understood when read in conjunction with the appended drawings. To the extent that the figures illustrate diagrams of the functional blocks of various embodiments, the functional blocks are not necessarily indicative of the division between hardware. It should be understood that the various embodiments are not limited to the arrangements and instrumentality shown in the drawings.

As used herein, an element or step recited in the singular and preceded with the word "a" or "an" should be understood as not excluding plural of said elements or steps, unless such exclusion is explicitly stated. Furthermore, references to "one embodiment" of are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide improved one-way and/or locking clutch mechanisms. Various examples provide smaller clutches than conventionally utilized and/or reduce or limit the amount of ferrous materials used. Additionally, various examples provide a lighter weight clutch, and/or reduce cost of clutches.

Various embodiments provide a one-way clutch that moves freely in one direction but is lockable in the other direction. Various embodiments control the rotation of an inner hub with respect to an outer hub by utilizing an interaction between a cam surface of an inner hub and a roller bearing interposed between the hubs. Further, various embodiments provide for a free range over which the cam surface and roller bearing interaction does not impede rotation of the hubs with respect to each other (e.g., via a recess in a surface of the outer hub).

A technical advantage of various embodiments includes improved performance of lockable clutches. A technical advantage of various embodiments includes inhibiting of rotation in a locked direction while allowing rotation in an unlocked direction. A technical advantage of various embodiments includes provision of a free range where rotation in both locked and unlocked directions is allowed.

Figure 1:
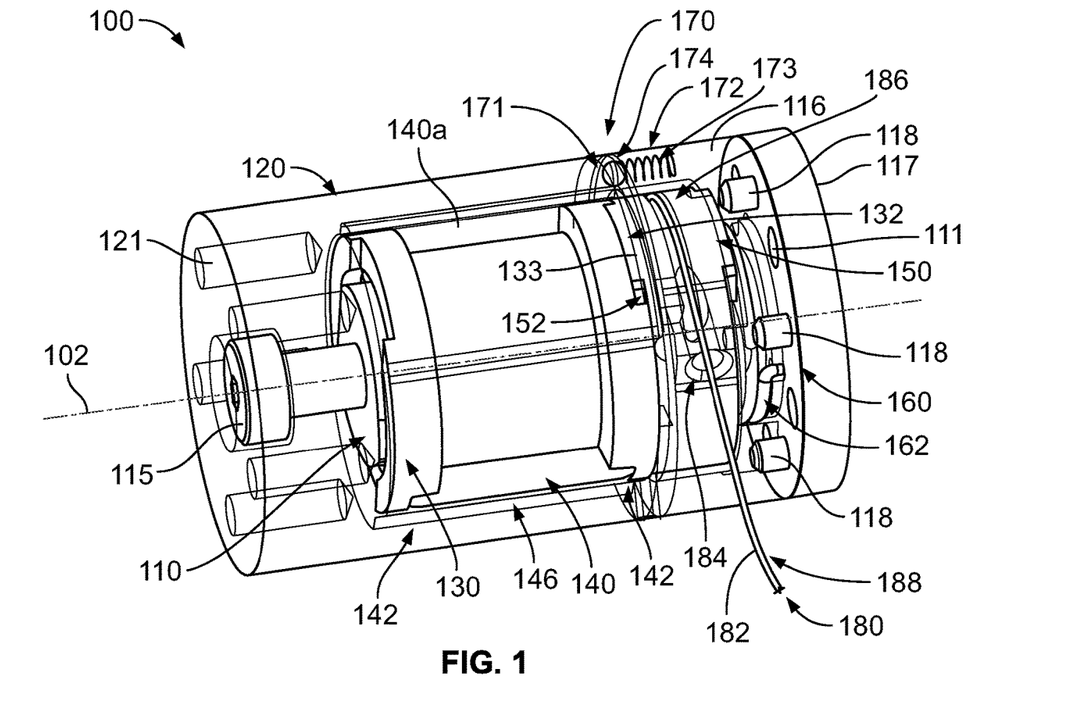
FIG. 1 provides a perspective view of a clutch assembly in accordance with various embodiments.

FIG. 1 provides a perspective view of a clutch assembly system 100 formed in accordance with various embodiments, and FIGS. 2-6 provide sectional views of the clutch assembly system 100 in various positions or configurations. Generally, the clutch assembly system 100 forms a cylindrical shape and is configured to control rotation of one or more components associated with the clutch assembly 100 about a hub axis 102.

As seen in FIGS. 1-6, the depicted clutch assembly 100 includes an inner hub 110, an outer hub 120, a roller cage 130, a roller bearing 140, a control collar 150, and a control collar positioning member 160. Generally, the various components of the clutch assembly 100 cooperate to control rotation of a structure mounted to the inner hub 110 with respect to a second structure mounted to the outer hub 120 (e.g., control rotation of a table arm with respect to a table bed). For example, fasteners 121 may be used to secure the outer hub 120 to an external structure (e.g., table bed), and fastener 111 may be used to secure the inner hub 110 to a different external structure (e.g., table arm configured to rotate with respect to table bed). Fastener 115 may be used to maintain the longitudinal position of the inner hub 110 relative to the outer hub 120. The clutch assembly 100 is configured to selectively permit or prevent rotation in various directions and/or over various ranges. For example, the control collar 150 may be moved between a first position (e.g., a locked position) in which rotation of the inner hub 110 with respect to the outer hub 120 is restricted (e.g., inhibited or prevented) in at least one direction, and a second position (e.g., an unlocked or free position) in which rotation is permitted or uninhibited. In various embodiments, each component of the clutch assembly 100 is made of non-ferrous material(s). Examples of material that may be used in non-ferrous or low ferrous configurations include 6061 aluminum alloy, 7075 aluminum alloy, 360 brass, 316 stainless steel, and 18-8 stainless steel. Accordingly, the clutch assembly 100 may be used in conjunction with magnetic resonance imaging (MRI) equipment or in other applications sensitive to the presence of ferrous material without adversely affecting performance.

The inner hub 110 is rotatable about the hub axis 102. The inner hub 110 includes a cam surface 112 that has a peak 113 and a bottom 114. (See FIGS. 2-6.) The illustrated embodiment also has a peak 113a and corresponding bottom 114a, with the peak 113a disposed 180 degrees from the peak 113. The peak 113 defines a portion of the cam surface 112 having a relative or local maximum radius (or radial distance from the hub axis 102), while the bottom 114 defines a portion of the cam surface 112 near the peak 113 and having a relative or local minimum radius (or radial distance from the hub axis 102). In the illustrated example, the cam surface 112 has a generally constant radius corresponding to the radius of the bottom 114, with the radius increasing from the bottom 114 to the peak 113.

The outer hub 120 is radially disposed about the hub axis 102, and is concentric with the inner hub 110. The outer hub 120 is disposed radially outward of the inner hub 110. For example, the outer hub 120 may define a hollow cylinder having a cavity in which the inner hub 110 is disposed. The inner hub 110 is rotatable about the hub axis 102 with respect to the outer hub 120. In some embodiment, the outer hub 120 may be coupled to a stationary structure and be referred to as a static hub, while the inner hub 110 is coupled to a structure that rotates with respect to the stationary structure that is coupled to the outer hub 120, with the inner hub 110 accordingly referred to as a dynamic hub. It may be noted, however, that in other embodiments, the outer hub 120 may be rotatable about a stationary inner hub 110, or both hubs may rotate, however at different rates or in different directions with respect to each other. It may be noted that the outer hub 120 is depicted transparently in FIG. 1 for clarity of illustration of components disposed radially inwardly of the outer hub 120.

The roller cage 130 is interposed between the inner hub 110 and the outer hub 120 along a portion of the length of the inner hub 110. Generally, the roller cage 130 is used to secure and support one or more roller bearings between the inner hub 110 and the outer hub 120. It may be noted that the roller cage 130 is omitted from FIGS. 2-6 for improved clarity of illustration of other components. In the illustrated example, the roller cage 130 defines a generally cylindrical structure disposed radially inward of the outer hub 120 and radially surrounding the inner hub 110. In the illustrated embodiment, the roller cage 130 includes a recess 132 that accepts a corresponding tab 133 of the control collar 150. The recess 132 is wider than the tab 133, resulting in a gap 152. Movement of the tab 133 against either end of the recess 132 rotates the roller cage 130 with respect to the inner hub 110, allowing the position of the roller bearing 140 to be moved with respect to the peak 113 of the cam surface 112 (e.g., to move between locked and unlocked positions), depending on the position of the control collar 150. Use of the gap 152 permits small, incidental, or accidental movements in the control collar 150 without affecting the position of the roller bearing 140 with respect to the peak 113.

The roller bearing 140 is disposed within the roller cage 130 and interposed between the inner hub 110 and outer hub 120. In the illustrated embodiment, ends 142 of the roller bearing 140 are inserted into the roller cage 130 to support and position the roller bearing 140. A middle portion 146 of the roller bearing 140 is interposed between the ends 142, with the middle portion 146 of the roller bearing contacting the cam surface 112 of the inner hub 110. The roller bearing 140 extends along and rotates about a bearing axis that extends generally parallel to the hub axis 102. The roller bearing 140 contacts the inner hub 110, and rotates with any relative movement of the inner hub 110 to the roller cage 130. The roller bearing 140 is coupled to the inner hub 110 at a predetermined position relative to the peak 113. For example, when the clutch assembly 100 is in a locked condition, the roller bearing 140 is disposed at a predetermined position relative to the peak 113 such that the roller bearing 140 impedes movement of the peak 113 toward the roller bearing 140, accordingly impeding rotation of the inner hub 110 in a corresponding direction. The roller bearing 140 may then be moved a sufficient distance from the peak 113 (e.g., by movement of the roller cage 130 caused by movement of the control collar 150) to place the clutch assembly 100 in an unlocked condition, allowing rotation of the inner hub 110. In the illustrated embodiment, the clutch assembly 100 includes a second roller bearing 140a disposed 180 degrees from the roller bearing 140. Use of multiple roller bearings allows for smaller individual loads on individual roller bearings, allowing, for example, for use of smaller bearings and more compact design. Because the roller bearing 140 is disposed in the roller cage 130 which may rotate about the hub axis 102, the roller bearing 140 may be understood as rotating about its own axis, and also capable of orbiting or rotating about the hub axis 102 (e.g., when the roller cage 130 is rotated about the hub axis 102).

The control collar 150 is coupled to the roller cage 130 and movable between a locked position and an unlocked position. Generally, the control collar 150 is used to rotate the roller cage 130 relative to the inner hub 110, thereby changing the position of the roller bearing 140 relative to the peak 113 of the cam surface 112. When the roller bearing 140 is sufficiently close to the peak 113, the control collar 150 is in the locked position. When the roller bearing 140 is sufficiently far from the peak 113, the control collar 150 is in the unlocked position.

Figure 2:
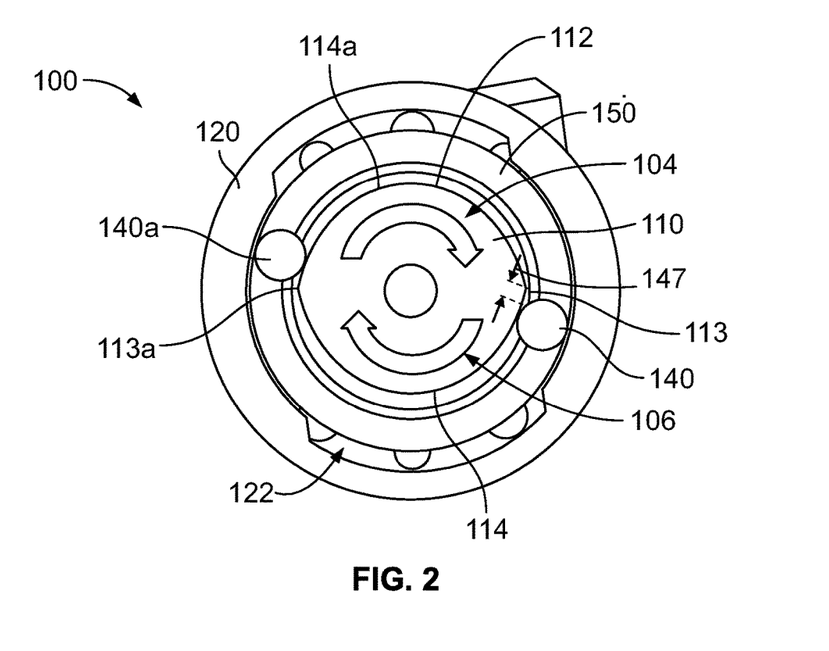
FIG. 2 provides a cross-sectional view of the clutch assembly of FIG. 1 showing locked and unlocked directions.

In the locked position (see, e.g., FIGS. 2-4), the roller bearing 140 is proximate the peak 113 (e.g., contacting the peak 113 or at a sufficiently small distance such that attempted rotation in a given direction of the cam surface 112 with respect to the roller bearing 140 results in an interaction between the roller bearing 140 and a portion of the cam surface 112 surrounding or neighboring the peak 113), such that rotation of the inner hub 110 relative to the outer hub 120 is inhibited (e.g., by an interaction between the peak 113 or surrounding portion of the inner hub 110 with the roller bearing 140) in a locked direction 104 but uninhibited in an unlocked direction 106. The locked direction 104 and unlocked direction 106 are opposite rotational directions. As seen in FIG. 2, which depicts the clutch assembly 100 in the locked position, the locked direction 104 is clockwise, and the unlocked direction 106 is counterclockwise. Generally, interaction between the roller bearing 140 and the peak 113 (or surrounding or neighboring portion of the cam surface 112) inhibits rotation in the locked direction 104 but not in the unlocked direction 106 when the clutch assembly 100 is in the locked position.

Figure 3:
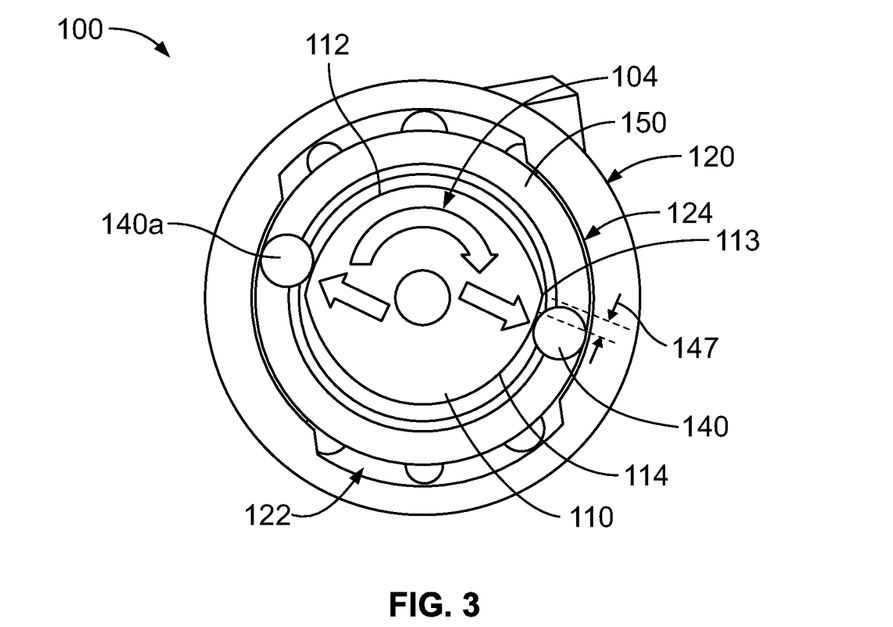
FIG. 3 provides a cross-sectional view of the clutch assembly of FIG. 1 in a locked position.
Figure 4:
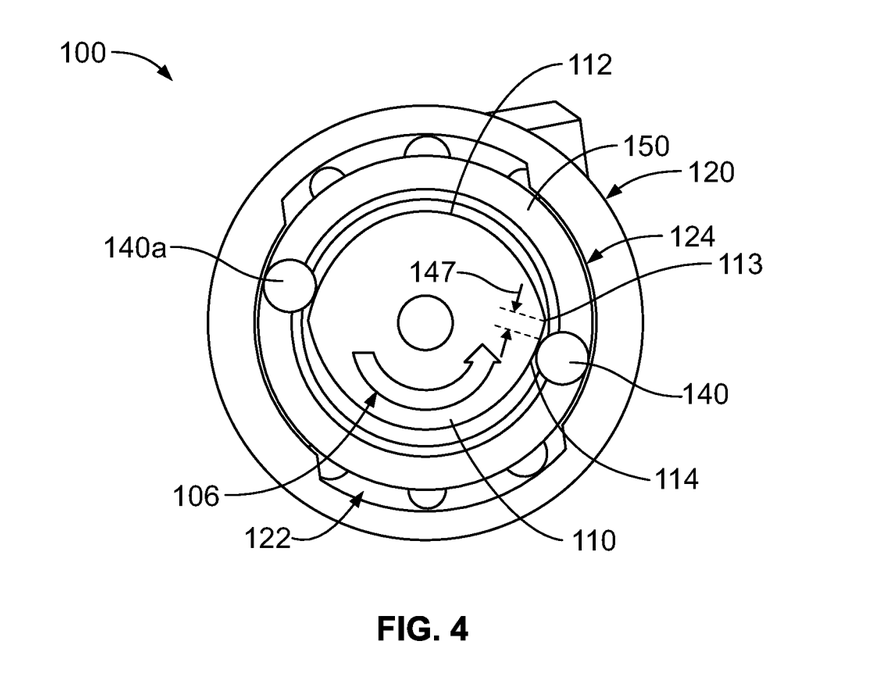
FIG. 4 provides a cross-sectional view of the clutch assembly of FIG. 1 in a locked position.
Figure 5:
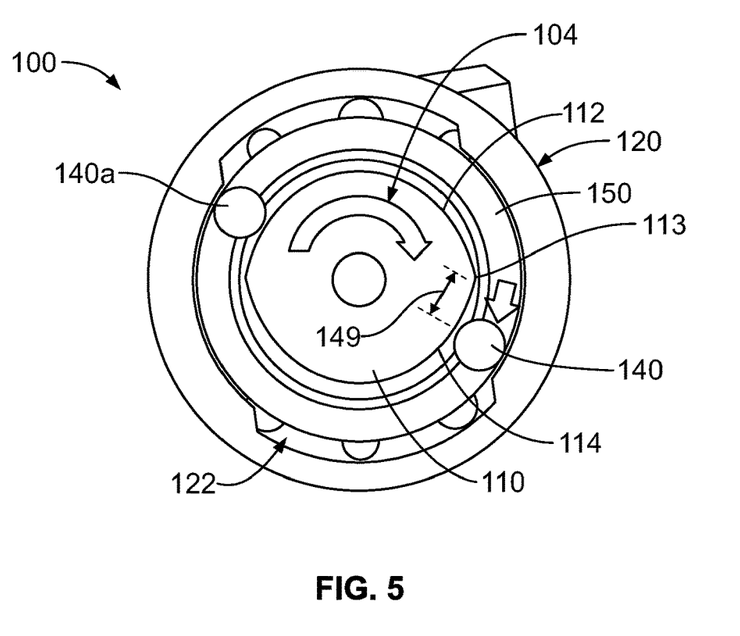
FIG. 5 provides a cross-sectional view of the clutch assembly of FIG. 1 in an unlocked position.

FIG. 3 depicts attempted rotation in the locked direction 104 when the clutch assembly 100 is in the locked position, and FIG. 4 depicts attempted rotation in the unlocked direction 106 when the clutch assembly 100 is in the locked position. As seen in FIG. 3, rotation of the inner hub 110 in the locked direction 104 (clockwise) moves the peak 113 toward the roller bearing 140, and causes an interaction between the peak 113 and the roller bearing 140. As the peak 113 (or surrounding or neighboring portion of the cam surface 112) pushes against the roller bearing 140, the roller bearing is supported in place by an inner surface 124 of the outer hub 120, thereby preventing rotation of the inner hub 110 in the locked direction 104. For example, the roller bearing 140 may be sufficiently pinched between the peak 113 (or neighboring portion of the cam surface 112) and the inner surface 124 of the outer hub 120 to prevent rotation of the roller bearing 140 about its own axis and accordingly inhibit rotation of the inner hub 110 about the hub axis 102. The size and location of the peak 113 as well as the diameter of the roller bearing 140 and relative positioning of the roller bearing 140 with respect to the peak 113 in the locked direction 104 may be selected or configured to provided sufficient resistance to rotation in the locked direction 104.

However, because of the relative positioning of the peak 113 and the roller bearing 140, the peak 113 and roller bearing 140 do not interact when the inner hub 110 is rotated in the unlocked direction 106 relative to the outer hub 120. As seen in FIG. 4, rotation in the unlocked direction 106 (counter-clockwise in the illustrated embodiment), moves the peak 113 away from the roller bearing 140 and allows rotation of the roller bearing 140 about its own axis. Accordingly, the inner hub 110 is not inhibited or impeded by the roller bearing 140 from rotating in the unlocked direction 106 relative to the outer hub 120.

In the unlocked position (see, e.g., FIG. 5), the roller bearing 140 is disposed a greater distance 149 from the peak 113 relative to the locked position, wherein rotation of the inner hub 110 relative to the outer hub 120 is not inhibited in the locked direction 104 or the unlocked direction 106. In the illustrated embodiment, to move the clutch assembly 100 from the locked position to the unlocked position, the roller cage 130 is rotated relative to the inner hub 110 via the control collar 150, resulting in the roller bearing 140 (which is held in the roller cage 130) orbiting about the hub axis 102 relative to the inner hub 110 to a position sufficiently far from the peak 113 such that the peak 113 (or surrounding or neighboring areas of the cam surface 112) does not interact with the roller bearing 140 to impede rotation in the locked direction 104. Additionally, the roller bearing 140 is sufficiently far from the peak 113 to allow the rotation of the roller bearing 140 about its own axis. Accordingly, the roller bearing 140 does not impede or inhibit rotation of the inner hub 110 relative to the outer hub 120 in either the locked direction 104 or the unlocked direction 106 when in the unlocked position. As seen in FIGS. 2-5, the distance 149 between the peak 113 and roller bearing 140 in the unlocked position (FIG. 5) is greater than the distance 147 between the peak 113 and the roller bearing 140 in the locked position (FIGS. 2-4).

With continued reference to FIG. 1, the control collar positioning member 160 couples the control collar to the inner hub 110, and urges the control collar 150 into the locked position. Accordingly, in a default state, the clutch assembly 100 is in the locked position (due to the action of the control collar positioning member 160), and the clutch assembly 100 may be moved to the locked position only via a force or input sufficient to overcome the control collar positioning member 160 (e.g., via a sufficiently strong manual input to the control collar 150). In the illustrated embodiment, the control collar positioning member 160 comprises a torsion spring 162 disposed about the hub axis 102 and configured to resiliently bias the control collar 150 toward the locked position.

In various embodiments, the clutch assembly 100 includes a free range over which rotation in either the locked direction 104 or unlocked direction 106 is allowed in either the locked or unlocked positions. For example, the clutch assembly 100 may be placed in the unlocked position, and then rotated into the free range. When in the free range, the clutch assembly 100 may be allowed to return to the locked position and still rotate in either the locked or unlocked direction, until the rotation brings the clutch assembly out of the free range.

Figure 6:
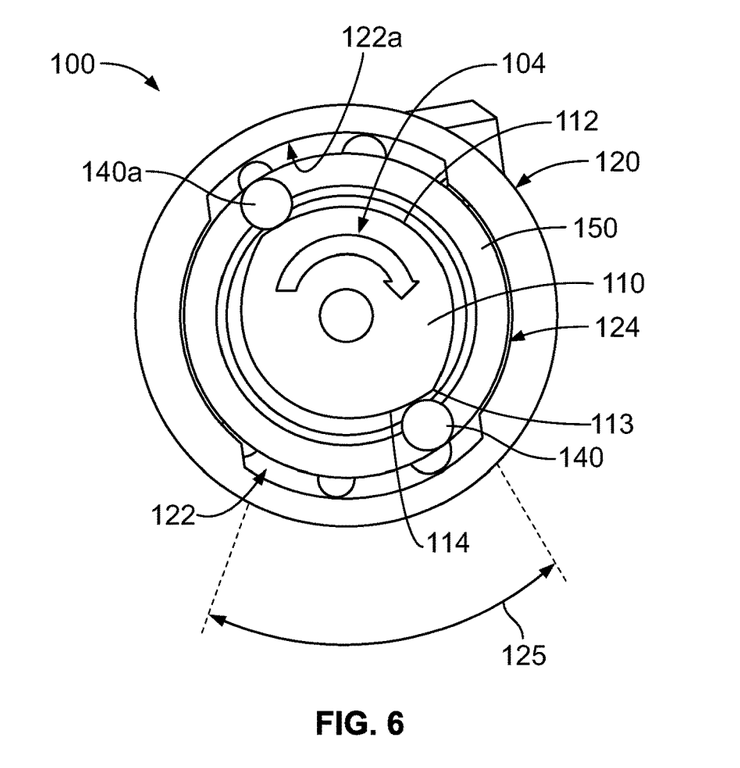
FIG. 6 provides a cross-sectional view of the clutch assembly of FIG. 1 with a roller bearing positioned over a free range.

FIG. 6 illustrates the clutch assembly 100 with the roller bearing 140 positioned over a free range 125. As seen in FIG. 6, the outer hub 120 comprises a recess 122 that extends into the inner surface 124 of the outer hub 120. The recess 122 defines a free range 125 in which the inner hub 110 is free to rotate relative to the outer hub 120 (e.g., not inhibited by interaction with the roller bearing 140). For example, with the roller bearing 140 disposed over the free range 125 defined by the recess 122, if the peak 113 of the inner hub 110 pushes against the roller bearing 140, the recess 122 results in the roller bearing 140 not having any contact with the inner surface 124, preventing any pinching of the roller bearing 140 and accordingly allowing the roller bearing 140 to be free to rotate about its axis, and allowing the inner hub 110 to rotate in either direction relative to the outer hub 120, even in the locked position in which the roller bearing 140 is proximate the peak 113. The size and positioning of the recess 122 may be selected or configured relative to provide a desired starting and ending points for a free range of rotation. In the illustrated embodiment, an additional recess 122a is disposed at 180 degrees to recess 122 to provide a corresponding free range for roller bearing 140a.

It may be noted that in various embodiments, additional mechanisms may be provided to help secure or maintain components of the clutch assembly 100 in one or more configurations or positions. For example, in the illustrated embodiment, as best seen in FIG. 1, the clutch assembly 100 includes a detent assembly 170. The detent assembly 170 couples the inner hub 110 and outer hub 120, and helps maintain the inner hub 110 and outer hub 120 in a predetermined position (or positions) relative to each other independent of whether the clutch assembly 100 is in the locked or unlocked position, and also independent of the direction of rotation. In the illustrated embodiment, the detent assembly 170 includes an outer hub recess 171, a base recess 172, a spring 173, and a ball 174. The spring 173 resiliently biases the ball 174 into a position where the ball 174 overlaps the intersection between the base recess 172 and the outer hub recess 171, causing an interference inhibiting rotation of the inner hub 110 relative to the outer hub 120. However, a sufficiently strong applied rotational force biases the ball 174 deeper into the base recess 172, removing the interference and allowing rotation. The detent assembly 170 helps prevent inadvertent, undesired, or accidental rotation of the inner hub 110 relative to the outer hub 120 in either direction, while still providing for quick, convenient movement when desired by a manual input. It may be noted that multiple recesses may be disposed about the hubs to accept one or more balls in predetermined default positions (e.g., every 90 degrees). In the illustrated embodiment, the base recess 172 extends into a hub base 116 (depicted as transparent in FIG. 1 for clarity of illustration of internal components) that is coupled to a flange 117 of the inner hub 110 via threaded fasteners 118. It may be noted that the torsion spring 162 is also mounted to the flange 117 in the illustrated embodiment.

With continued reference to FIG. 1, the illustrated clutch assembly 100 includes a control collar actuation assembly 180 coupled to the control collar 150. The control collar actuation assembly 180 is configured to urge the control collar to the unlocked position. For example, the illustrated example includes a wire rope 182 passing through a collar opening 184 of the hub base 116 and having an end 186 coupled to the control collar 150. An operator may provide a manual input to the wire rope 182 (e.g., by pulling on free end 188 of the wire rope 182) sufficient to exceed a force provided by the torsion spring 162, causing rotation of the control collar 150. Once the control collar 150 rotates a sufficient distance to eliminate the gap 152, continued rotation of the control collar 150 causes rotation of the roller cage 130 relative to the inner hub 110 to move the clutch assembly from the locked position toward the unlocked position. Upon removal of the manual input (e.g., release of the wire rope 182), the torsion spring 162 acts to return the clutch assembly 100 to the locked position. It should be noted an alternative arrangement is possible where the control collar positioning member 160 is configured to bias the control collar 150 toward the unlocked position. In this arrangement the manual operator input to the wire rope 182 moves the clutch assembly from the unlocked position to the locked position.

In various examples, the clutch assembly 100 may be used in connection with medical equipment. For example, the clutch assembly 100 may be used in connection with an arm that is rotatable to a bed. The clutch assembly 100 may be configured to provide rotational positional control to help control movement of the arm relative to the bed and to help position the arm in one or more predetermined positions (e.g., generally parallel to the bed for support of an arm for imaging, generally perpendicular to the bed to secure a patient in place on the bed, at a declined position for loading or unloading, etc.). The clutch assembly 100 may be configured to provide desired locking and free ranges as well desired locked and unlocked directions of rotations to provide the desired functionality for the arm for a given application.

Figure 7:
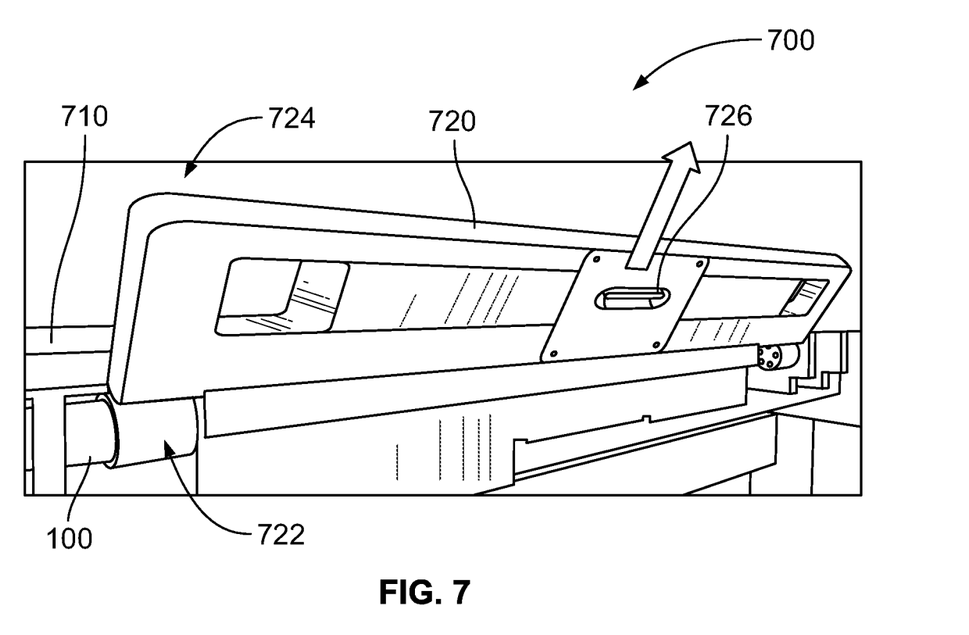
FIG. 7 provides a perspective view of an MRI table assembly in accordance with various embodiments.

FIG. 7 depicts an example MRI table assembly 700 including a table bed 710, table arm 720, and clutch assembly 100. The table arm 720 is rotatably coupled to the table bed 710 via the clutch assembly 100, which may be generally similar in various respect to the clutch assembly 100 discussed herein. The table arm 720 has a first end 722 that is coupled to the clutch assembly 100 and a second end 724 that is free. The table arm is coupled to the inner hub 110 and the table bed 710 is coupled to the outer hub 120, so that the rotation of the inner hub 110 relative to the outer hub 120 controls the position of the table arm 720 relative to the table bed 710. In the illustrated embodiment, the table arm 720 includes a movable handle 726. Movement of the movable handle 726 in a given direction (e.g., upward) may be used to move the clutch assembly 100 from the locked position to the unlocked position. For example, the movable handle 726 may be coupled to the wire rope 182 such that pulling on the movable handle 726 causes the wire rope 182 to rotate the control collar 150 from the locked position to the unlocked position, providing a convenient way for an operator to select the locked or unlocked positions. It may be noted that one or more detent assemblies (e.g., detent assembly 170) may be used independently of the bearing/peak interaction to provide additional positioning functionality. In an alternative arrangement, the table arm is coupled to the outer hub 120 and the table bed 710 is coupled to the inner hub 110. In this arrangement the movable handle 726 is positioned on the table bed 710.

Figure 8:
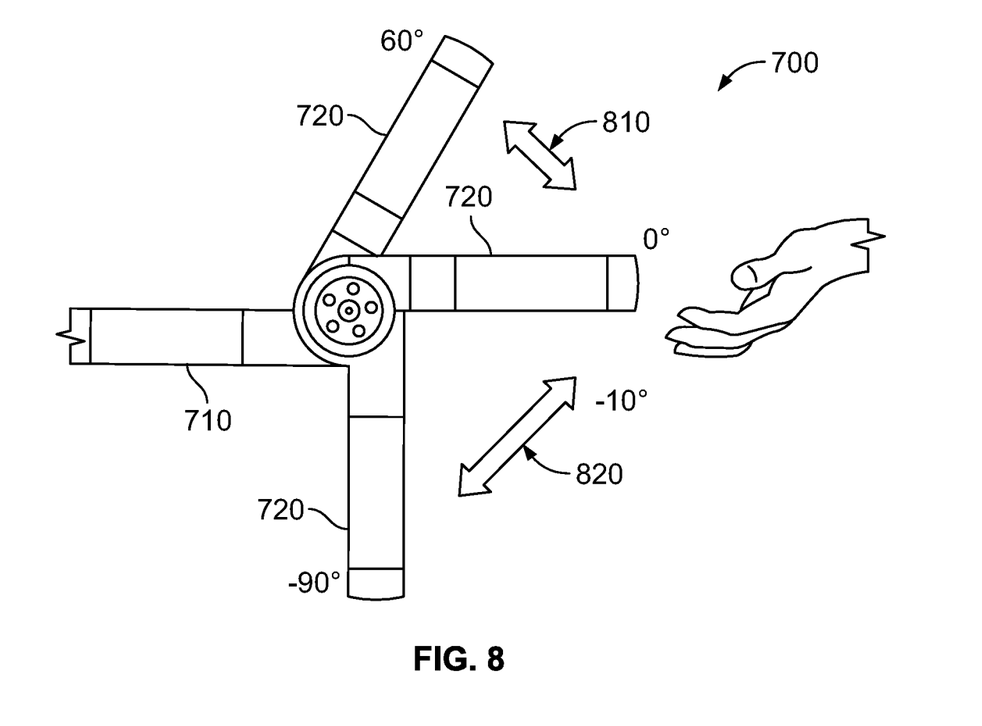
FIG. 8 illustrates positioning ranges for the MRI table assembly of FIG. 7.

As discussed above, the clutch assembly 100 may be configured to provide desired locking and free ranges as well as desired locked and unlocked directions of rotations to provide the desired functionality for positioning of the table arm 720 relative to the table bed 710. For example, FIG. 8 illustrates positioning ranges for the MRI table assembly of FIG. 7. As seen in FIG. 8, the ranges include a locking range 810 and a free range 820. In the illustrated embodiment, the locking range 810 extends from about horizontal in a counter clockwise direction to about 60 degrees. The free range 820 extends in clockwise direction to about minus 90 degrees. The particular beginning and end points as well as length of any given range may be provided by appropriate configuration of the clutch assembly (e.g., positioning of recesses 122 in outer hub 120).

Figure 9:
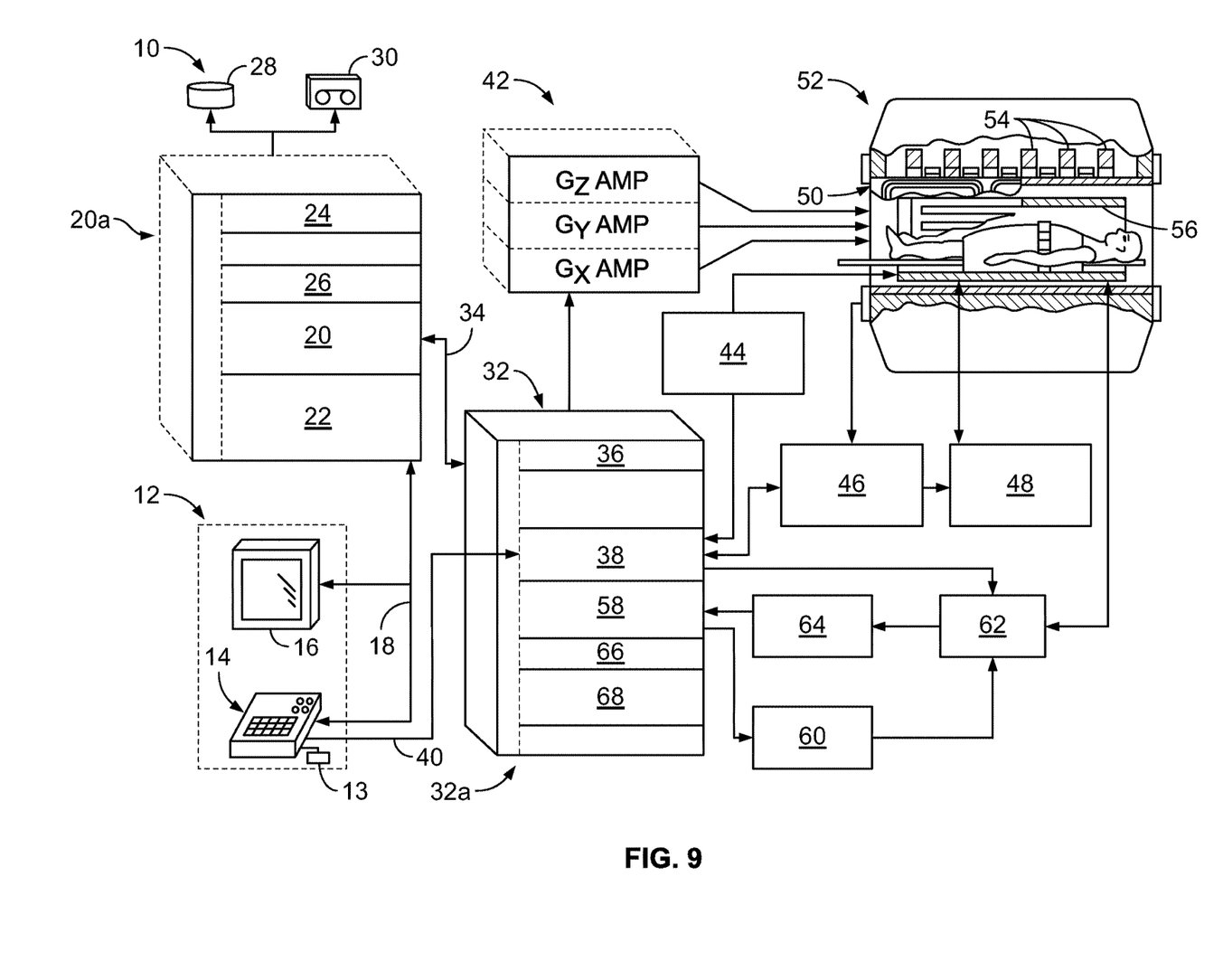
FIG. 9 provides a schematic view of a magnetic resonance imaging (MRI) system in accordance with various embodiments.

As discussed herein various methods and/or systems (and/or aspects thereof) described herein may be implemented in connection with an MRI system. For example, FIG. 9 depicts various major components of an MRI system 10 formed in accordance with various embodiments. In various embodiments, the MRI system 10 may include a table assembly 700 generally similar in respects to the table assembly 700 discussed herein. The operation of the system is controlled from an operator console 12 which includes a keyboard or other input device 13, a control panel 14, and a display 16. The console 12 communicates through a link 18 with a separate computer system 20 that enables an operator to control the production and display of images on the screen 16. The computer system 20 includes a number of modules which communicate with each other through a backplane 20a. These include an image processor module 22, a CPU module 24 and a memory module 26, known in the art as a frame buffer for storing image data arrays. The computer system 20 is linked to disk storage 28 and recordable media 30 for storage of image data and programs, and communicates with a separate system control 32 through a high speed serial link 34. The input device 13 can include a mouse, joystick, keyboard, track ball, touch activated screen, light want, voice control, or any similar or equivalent input device, and may be used for interactive geometry prescription.

The system control 32 includes a set of modules connected together by a backplane 32a. These include a CPU module 36 and a pulse generator module 38 which connects to the operator console 12 through a serial link 40. It is through link 40 that the system control 32 receives commands from the operator to indicate the san sequence that is to be performed. The pulse generator module 38 operates the system components to carry out the desired scan sequence and produce data which indicates the timing, strength and shape of the RF pulses produced, and the timing and length of the data acquisition window. The pulse generator module 38 connects to a set of gradient amplifiers 42, to indicate the timing and shape of the gradient pulses that are produced during the scan. The pulse generator module 38 can also receive patient data from a physiological acquisition controller 44 that receives signals from a number of different sensor connected to the patient or subject, such as ECG signals from electrodes attached to the patient. And finally, the pulse generator module 38 connects to a scan room interface circuit 46 which receives signals from various sensors associated with the condition of the patient and the magnet system. It is also through the scan room interface circuit 46 that a patient positioning system 48 receives commands to move the patient to the desired position for the scan.

The gradient waveforms produced by the pulse generator module 38 are applied to the gradient amplifier system 42 having $G_x$, $G_y$, and $G_z$ amplifiers. Each gradient amplifier excites a corresponding physical gradient coil in a gradient coil assembly 50 generally designated to produce the magnetic field gradients used for spatially encoding acquired signals. The gradient coil assembly 50 and RF shield (not shown) form a part of a magnet assembly 52 which includes a polarizing magnet 54 and a RF coil assembly 56. A transceiver module 58 in the system control 32 produces pulses which are amplified by an RF amplifier 60 and coupled to the RF coil assembly 56 by a transmit/receive switch 62. The resulting signals emitted by the excited nuclei in the patient may be sensed by the same RF coil assembly 56 or apportion thereof and coupled through transmit/receive switch 62 to a preamplifier 64. The amplified MR signals are demodulated, filtered, and digitized in the receive section of the transceiver 58. The transmit/receive switch 62 is controlled by a signal from the pulse generator module 38 to electrically connect the RF amplifier 60 to the coil assembly 56 during the transmit mode and to connect the preamplifier 64 to the coil assembly 56 during the receive mode. The transmit/receive switch 62 can also enable a separate RF coil (for example, a surface coil) to be used in either the transmit or receive mode. The magnet assembly 52 may be cooled cryogenically.

The MR signals picked up by the selected RF coil are digitized by the transceiver module 58 and transferred to a memory module 66 in the system control 32. A scan is complete when an array of raw k-space data has been acquired in the memory module 66. This raw k-space data is rearranged into separate k-space data arrays for each image to be reconstructed, and each of these is input to an array processor 68 which operates to Fourier transform the data into an array of image data. This image data is conveyed through the serial link 34 to the computer system 20 where it is stored in memory, such as disk storage 28. In response to commands received from the operator console 12, this image data may be archived in long term storage, such as on the tape drive 30, or it may be further processed by the image processor 22 and conveyed to the operator console 12 and presented on the display 16.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation. For example, a processing unit, processor, or computer that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

It is to be understood that the above description is intended to be illustrative, and not restrictive. For example, the above-described embodiments (and/or aspects thereof)

may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f) unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal language of the claims.

What is claimed is:

1. A clutch assembly comprising:
   an inner hub rotatable about a hub axis, the inner hub comprising a cam surface comprising a peak and a bottom;
   an outer hub concentric with and disposed radially outward of the inner hub, the inner hub rotatable about the hub axis with respect to the outer hub;
   a roller bearing interposed between the inner and outer hub, the roller bearing coupled to the inner hub at a predetermined position relative to the peak; and
   a control collar configured to move the roller bearing between a locked position and an unlocked position, wherein:
      in the locked position, the roller bearing is proximate the peak, wherein rotation of the inner hub relative to the outer hub is inhibited in a locked direction but uninhibited in an unlocked direction,
      in the unlocked position, the roller bearing is disposed a greater distance from the peak relative to the locked position, wherein rotation of the inner hub relative to the outer hub is not inhibited in the locked direction or the unlocked direction.

2. The clutch assembly of claim 1, further comprising a control collar positioning member coupling the control collar to the inner hub and urging the control collar into the locked position, the control collar positioning member comprising a torsion spring disposed about the hub axis.

3. The clutch assembly of claim 1, comprising two roller bearings disposed 180 degrees apart from each other.

4. The clutch assembly of claim 1, further comprising a recess extending into an inner surface of the outer hub, the recess defining a free range in which the inner hub is free to rotate relative to the outer hub.

5. The clutch assembly of claim 1, further comprising a detent assembly coupling the inner hub and outer hub.

6. The clutch assembly of claim 1, further comprising a control collar actuation assembly coupled to the control collar and configured to urge the control collar to the unlocked position.

7. The clutch assembly of claim 1, further comprising a roller cage interposed between the inner hub and the outer hub, the roller bearing disposed within the roller cage, the control collar coupled to the roller cage and configured to rotate the roller cage relative to the hub axis.

8. A clutch assembly comprising:
   an inner hub rotatable about a hub axis, the inner hub comprising a cam surface comprising a peak and a bottom;
   an outer hub concentric with and disposed radially outward of the inner hub, the inner hub rotatable about the hub axis with respect to the outer hub, the outer hub having a recess extending into an inner surface of the outer hub, the recess defining a free range in which the inner hub is free to rotate relative to the outer hub;
   a roller bearing interposed between the inner and outer hub, the roller bearing coupled to the inner hub at a predetermined position relative to the peak; and
   a control collar configured to move the roller bearing between a locked position and an unlocked position, wherein:
      in the locked position, the roller bearing is proximate the peak, wherein rotation of the inner hub relative to the outer hub is inhibited in a locked direction but uninhibited in an unlocked direction,
      in the unlocked position, the roller bearing is disposed a greater distance from the peak relative to the locked position, wherein rotation of the inner hub relative to the outer hub is not inhibited in the locked direction or the unlocked direction.

9. The clutch assembly of claim 8, further comprising a control collar positioning member coupling the control collar to the inner hub and urging the control collar into the locked position, the control collar positioning member comprising a torsion spring disposed about the hub axis.

10. The clutch assembly of claim 8, comprising two roller bearings disposed 180 degrees apart from each other.

11. The clutch assembly of claim 8, further comprising a detent assembly coupling the inner hub and outer hub.

12. The clutch assembly of claim 8, further comprising a control collar actuation assembly coupled to the control collar and configured to urge the control collar to the unlocked position.

13. The clutch assembly of claim 8, further comprising a roller cage interposed between the inner hub and the outer hub, the roller bearing disposed within the roller cage, the control collar coupled to the roller cage and configured to rotate the roller cage relative to the hub axis.

14. A medical imaging table assembly comprising:
   a table bed;
   a table arm rotatably coupled to the table bed; and
   a clutch assembly rotatably coupling the table arm to the table bed, the clutch assembly comprising:
      an inner hub rotatable about a hub axis, the inner hub comprising a cam surface comprising a peak and a bottom;

an outer hub concentric with and disposed radially outward of the inner hub, the inner hub rotatable about the hub axis with respect to the outer hub;

a roller bearing interposed between the inner and outer hub, the roller bearing coupled to the inner hub at a predetermined position relative to the peak; and a control collar configured to move the roller bearing between a locked position and an unlocked position, wherein:

in the locked position, the roller bearing is proximate the peak, wherein rotation of the inner hub relative to the outer hub is inhibited in a locked direction but uninhibited in an unlocked direction, in the unlocked position, the roller bearing is disposed a greater distance from the peak relative to the locked position, wherein rotation of the inner hub relative to the outer hub is not inhibited in the locked direction or the unlocked direction.

15. The table assembly of claim 14, further comprising a control collar positioning member coupling the control collar to the inner hub and urging the control collar into the locked position, the control collar positioning member comprising a torsion spring disposed about the hub axis.

16. The table assembly of claim 14, comprising two roller bearings disposed 180 degrees apart from each other.

17. The table assembly of claim 14, further comprising a recess extending into an inner surface of the outer hub, the recess defining a free range in which the inner hub is free to rotate relative to the outer hub.

18. The table assembly of claim 14, further comprising a detent assembly coupling the inner hub and outer hub.

19. The table assembly of claim 14, further comprising a control collar actuation assembly coupled to the control collar and configured to urge the control collar to the unlocked position.

20. The table assembly of claim 14, further comprising a roller cage interposed between the inner hub and the outer hub, the roller bearing disposed within the roller cage, the control collar coupled to the roller cage and configured to rotate the roller cage relative to the hub axis.

* * * * *